Figure 1A:
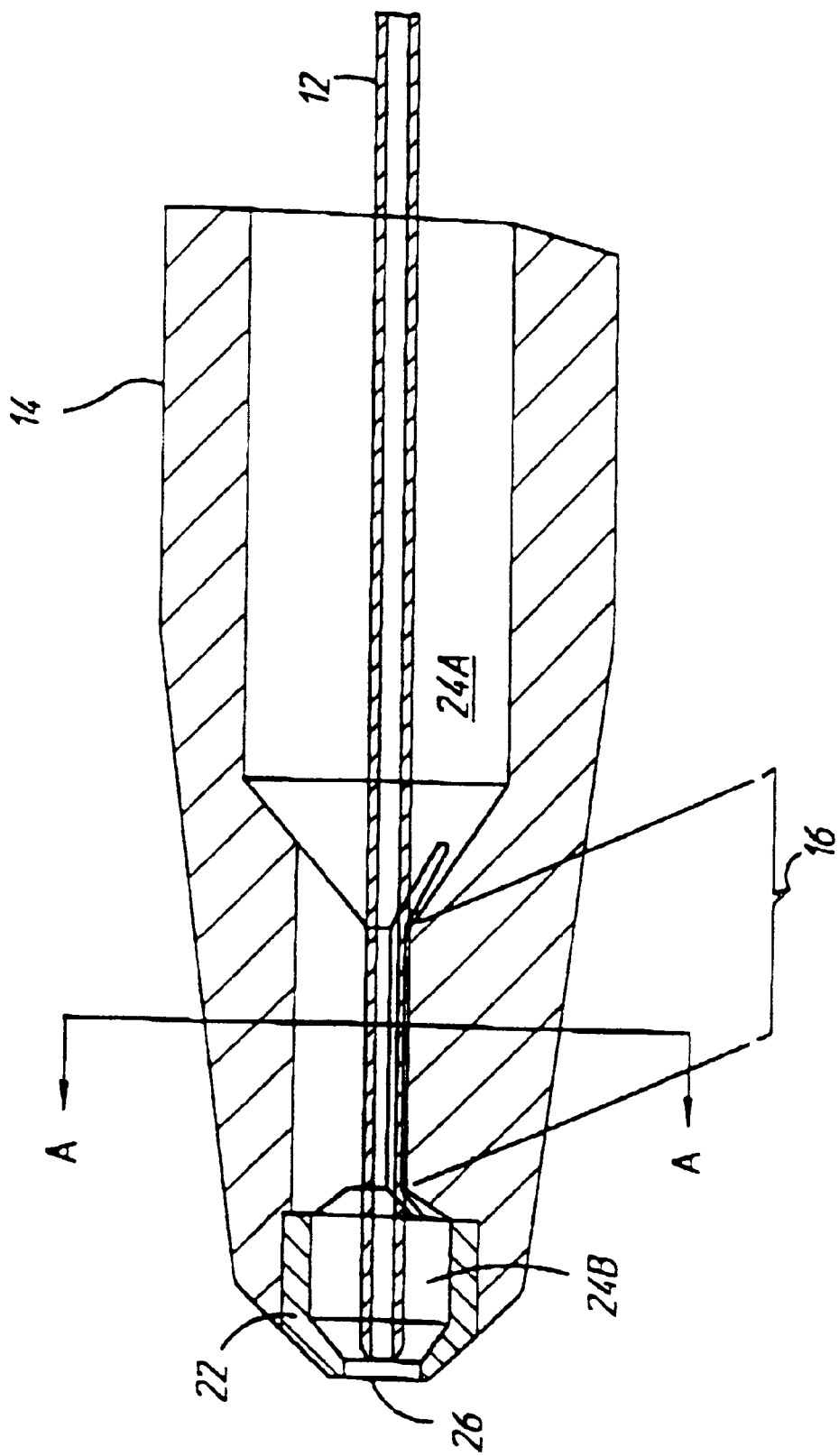

United States Patent [19]
Bertsch et al.

[11] Patent Number: 6,032,876
[45] Date of Patent: Mar. 7, 2000

[54] APPARATUS FOR FORMING LIQUID DROPLETS HAVING A MECHANICALLY FIXED INNER MICROTUBE

[75] Inventors: James L. Bertsch, Palo Alto; Steven M. Fischer, Hayward; Darrell L. Gourley, San Francisco; Harvey D. Loucks, Jr., La Honda, all of Calif.; Hans-Peter Zimmerman, Karsruhe, Germany

[73] Assignee: Hewlett-Packard Company, Palo Alto, Calif.

[21] Appl. No.: 09/203,907

[22] Filed: Dec. 1, 1998

Related U.S. Application Data

[63] Continuation of application No. 08/722,644, Sep. 27, 1996, Pat. No. 5,868,322, which is a continuation-in-part of application No. 08/593,319, Jan. 31, 1996, abandoned.

[51] Int. Cl.[7] .................................................. F23D 11/10
[52] U.S. Cl. ........................ 239/418; 234/423; 234/424; 73/864.81
[58] Field of Search ............................... 239/418, 423, 239/424, 433, 434; 73/864.81

[56] References Cited

U.S. PATENT DOCUMENTS

| | | | |
|---|---|---|---|
| 4,284,242 | 8/1981 | Randell | 239/423 |
| 4,531,056 | 7/1985 | Labowsky et al. | 250/288 |
| 5,322,510 | 6/1994 | Lindner et al. | 604/82 |
| 5,752,663 | 5/1998 | Fischer et al. | 239/424 |
| 5,868,322 | 2/1999 | Loucks, Jr. et al. | 239/418 |
| 5,884,846 | 3/1999 | Tan | 239/424 |

*Primary Examiner*—Andres Kashnikow
*Assistant Examiner*—Lisa Douglas

[57] ABSTRACT

The invention relates to an apparatus for forming liquid droplets, such as a micro nebulizer, useful for preparing samples for subsequent analysis via MS, AA, ICP, CE/MS, and similar analytical systems. The apparatus has a mechanically stabilized inner microtube or needle, thereby ensuring controllably uniform droplet size. The mechanical stabilization is provided by securing the inner microtube or needle, such as by narrowing the inner diameter of the outer microtube or otherwise narrowing the annular intermediate space between the inner and outer microtubes for a predetermined length. Thus, the inner microtube is secured in a centered or otherwise predetermined fixed radial position, with minimum perturbation of the fluid flow. Further, a tip, when coupled with the exit end of the outer microtube, provides a region in which the sheath fluid flow in the outer microtube stabilizes prior to both exiting the tip and colliding with the liquid analyte exiting the inner microtube.

6 Claims, 13 Drawing Sheets

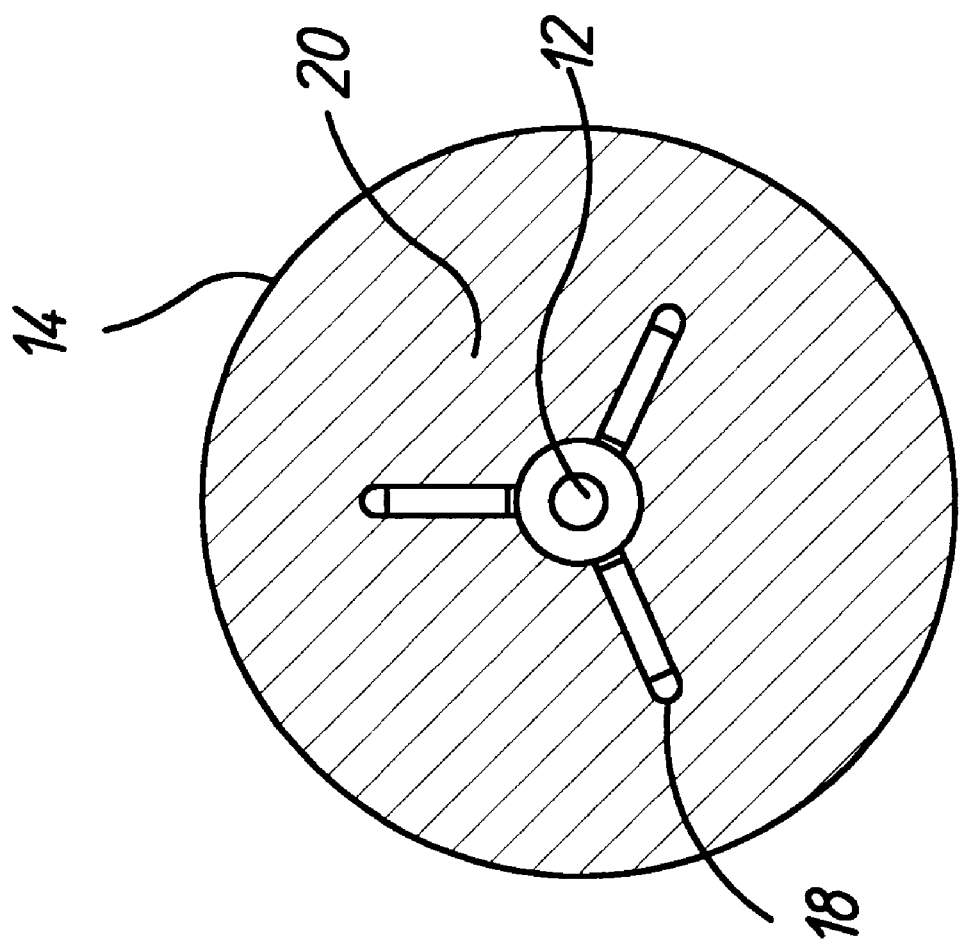

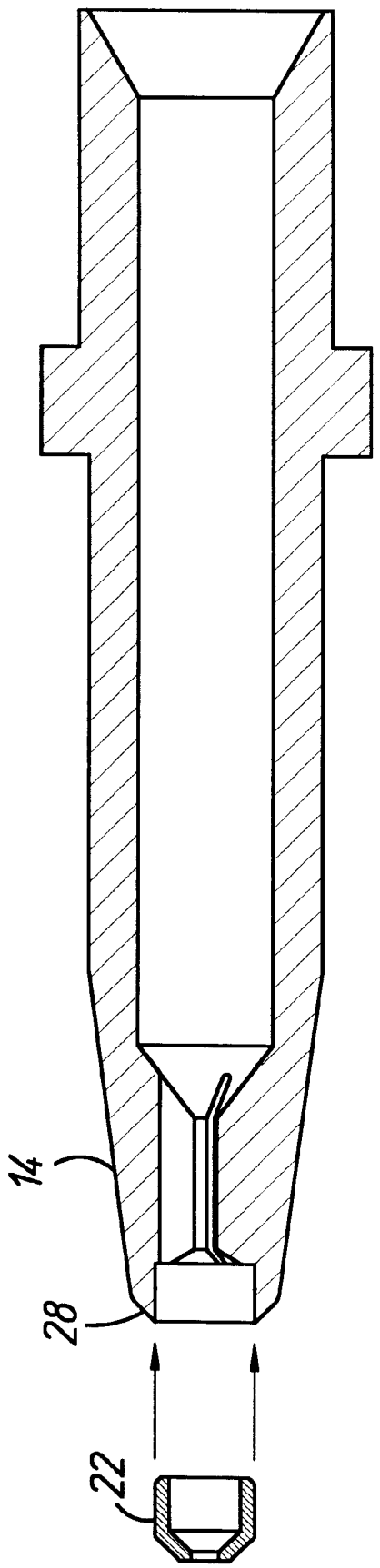

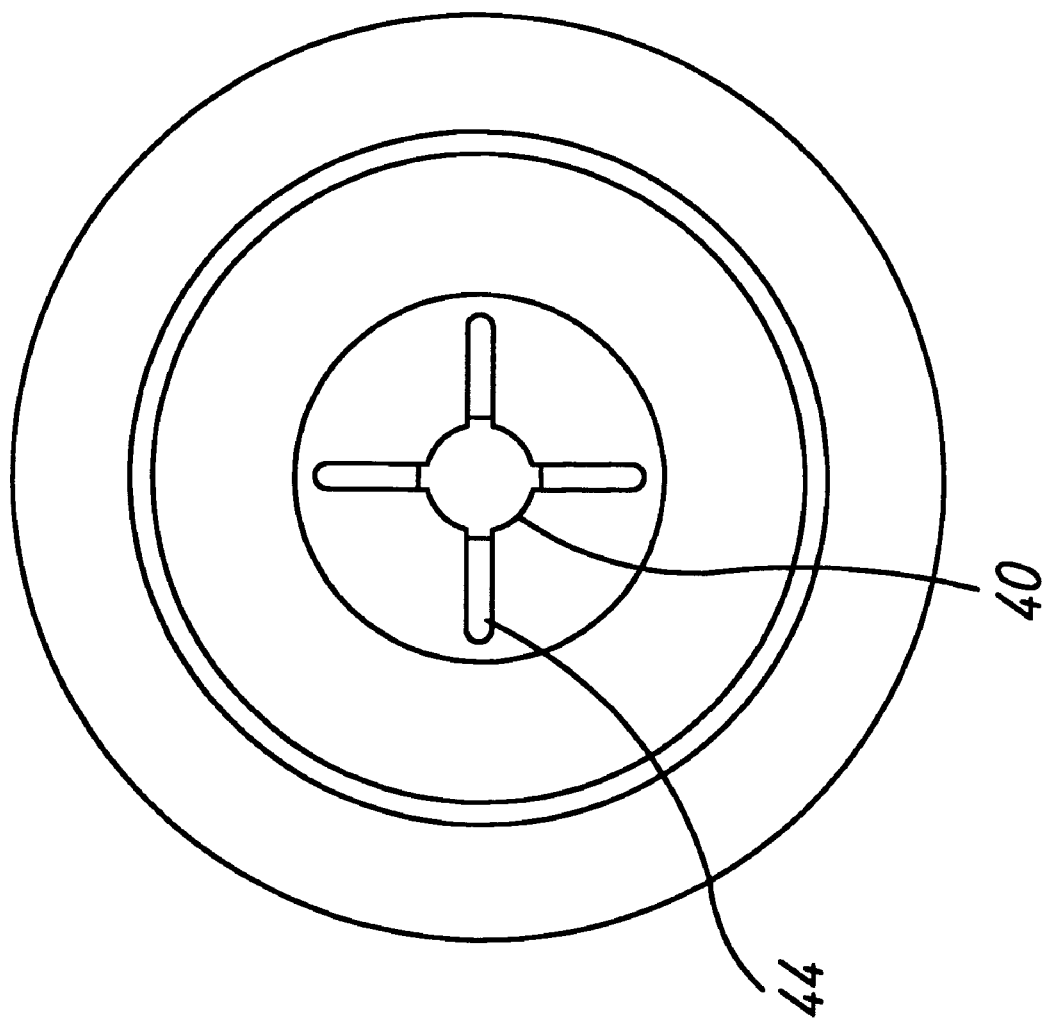

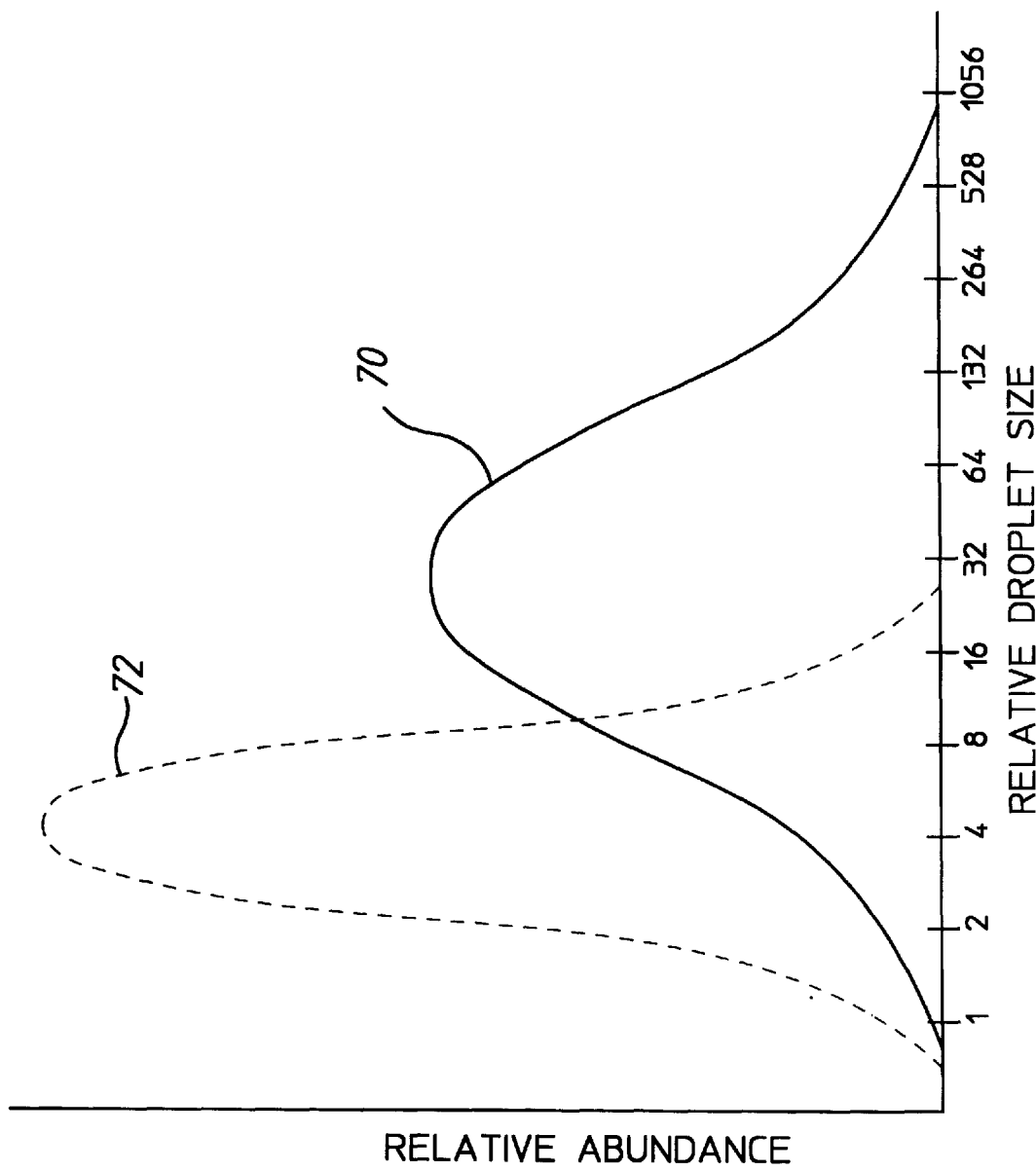

APPARATUS FOR FORMING LIQUID DROPLETS HAVING A MECHANICALLY FIXED INNER MICROTUBE

This is a continuation of application Ser. No. 08/722,644 filed on Sep. 27, 1996, U.S. Pat. No. 5,868,322, which was a continuation-in-part of application Ser. No. 08/593,319 filed on Jan. 31, 1996, abandoned.

FIELD OF INVENTION

This invention relates generally to apparatus for forming liquid droplets, such as liquid sprayers, atomizers, and the like. More particularly, this invention relates to nebulizers useful in liquid chromatography (LC) or capillary electrophoresis (CE) coupled with an analytical system, such as a mass spectrometer (MS).

BACKGROUND

Micro nebulizers have been used to convert liquid samples to fine droplets suitable for analysis. Micro nebulizers provide a useful interface for analytical systems based on techniques such as mass spectrometry (MS), atomic absorption (AA), or inductively coupled plasma (ICP) which cannot directly analyze liquid samples. In such analytical systems, the liquid sample must first be converted to a gas. The ideal conversion would, theoretically, involve spraying the liquid into uniform fine droplets. The uniform fine droplets then would then be dried and converted to a gas suitable for analysis. In practice, uniform fine droplets are difficult to attain. If droplets vary in size, the heat necessary to dry a larger droplet damages the analyte in a finer droplet. Large droplets, if left undried, result in noise and signal interference.

Current nebulizers rely on a concentric microtube arrangement to spray liquid samples into droplets. The inner microtube carries the liquid sample; the outer microtube carries an inert fluid (liquid or gas) used as a sheath fluid. At the exits of the concentric microtubes, the liquid sample and the sheath fluid collide and the liquid sample is broken into droplets by the shearing force of the sheath fluid. Uniform laminar sheath fluid flow is critical to producing uniform size droplets. Any imperfections in the annular region between the inner and outer microtubes forming the sheath fluid flow region create turbulence in the sheath fluid, which translates directly into lack of control of droplet size and uniformity. Such imperfections may be generated, for example, by transition points within the sheath fluid flow region such as at the point the sheath fluid is introduced into the outer microtube.

To compensate for such imperfections in current nebulizer microtubes, nebulizers with microtubes of relatively great length have been used. The increase in microtube length (in some cases up to 25 mm or more) permits the sheath fluid to stabilize after the turbulence induced by internal imperfections in the sheath fluid entry point transition. However, increased microtube length alone fails to solve the problem entirely or even satisfactorily. Long microtubes dissipate the energy needed for the shearing force collision of sheath fluid and the liquid sample. More problematic is that long concentric microtubes do not stay centered relative to each other; thus, the exit aperture experienced by the sheath fluid is either asymmetrical, changes with time, or both. As a result, the velocity and shearing force of the sheath fluid experienced by the liquid sample is unevenly distributed and changes with time, which brings about the problem that plagues current nebulizers: namely, variation in size and uniformity of the droplets produced.

What is needed is a nebulizer that reproducibly generates uniform fine droplets of controllable size and distribution. Further, what is needed is a nebulizer wherein the aperture experienced by the sheath fluid is controllable. Also desirable is a nebulizer wherein the inner microtube or needle is mechanically stabilized and wherein such stabilizer elements do not substantially impede the sheath fluid flow in the outer microtube. Further, what is needed is a nebulizer wherein the sheath fluid flow path is sufficiently short and smooth such that the reduction of energy associated with liquid droplet formation occurs substantially at or near the point of nebulization.

SUMMARY OF THE INVENTION

In one embodiment, the invention provides an apparatus for forming droplets from a liquid comprising:

A. at least one inner microtube having an outer wall, an exit end, and an exit end aperture, B. an outer microtube having an inner wall, an exit end, and an exit end aperture, wherein the inner microtube has an outer diameter smaller than the inner diameter of the outer microtube, and the inner microtube is positioned within and is surrounded by the outer microtube such that an annular intermediate space is formed therebetween, with the exit end of each microtube being located at a same end of the apparatus, C. one or more intermediate structures either (i) extending inward radially from the inner wall of the outer microtube and contacting the outer wall of the inner microtube for a predetermined length, (ii) extending outward radially from the outer wall of the inner microtube and contacting the inner wall of the outer microtube for a predetermined length, or (iii) spanning the annular intermediate space and contacting both the outer wall of the inner microtube and the inner wall of the outer microtube for a predetermined length, wherein the intermediate structure is situated so as to mechanically stabilize the inner microtube, and D. one or more communicating channels continuing lengthwise along the outside of the inner microtube, wherein the communicating channel provides a continuation of the annular intermediate space and through which a fluid may continue to flow after encountering the intermediate structure.

In a preferred embodiment, the invention provides a nebulizer assembly, comprising:

A. at least one inner microtube having an exit end and an exit end aperture,

B. an outer microtube having an exit end adapted for coupling with a tip and an exit end aperture, wherein the inner microtube has an outer diameter smaller than the inner diameter of the outer microtube, and the inner microtube is positioned within and is surrounded by the outer microtube such that an annular intermediate space is formed therebetween, with the exit end of each microtube being located at a same end of the nebulizer assembly, and C. a tip which couples with a surface at the exit end of the outer microtube, thereby forming a region near the exit ends of the microtubes within which fluid flow may stabilize; wherein the inner diameter of the outer microtube is narrowed for a predetermined portion of its length such that the annular intermediate space is reduced to one or more fluid communicating channels.

In one embodiment, two or more inner microtubes are included within the apparatus or nebulizer assembly, such that multiple annular intermediate spaces for fluid flow are formed.

The invention provides an apparatus such as a nebulizer that reproducibly generates uniform droplets of controllable size and distribution. Further, the invention provides an apparatus wherein the aperture experienced by the sheath fluid is controllable. The invention further provides an apparatus wherein the inner microtube or needle is mechanically stabilized and wherein such stabilizer elements do not substantially impede sheath fluid flow in the outer microtube. Further, the apparatus taught herein provides a sheath fluid flow path which is sufficiently short and smooth such that the reduction of energy associated with liquid droplet formation occurs substantially at or near the point of nebulization.

The apparatus described above may be coupled to any analytical system in order that droplets produced by the apparatus may be analyzed. In a preferred embodiment, the apparatus is coupled to a mass spectrometer. The invention is particularly useful as part of an interface for mass spectrometers employing, for example, electrospray ionization (ESI) or atmospheric pressure chemical ionization (APCI) to analyze liquid samples.

BRIEF DESCRIPTION OF THE DRAWINGS

FIG. 1, A through C, schematically illustrates a nebulizer assembly according to the present invention.

FIG. 1A is an enlarged schematic of the inner stabilizer portion of a nebulizer;

FIG. 1B is a cross section of the nebulizer of FIG. 1A taken along axis AA; and FIG. 1C is an enlarged view of the tip of the nebulizer assembly of FIG. 1A.

FIG. 2 illustrates the tip and outer microtube components of an embodiment of the invention taught herein.

FIG. 3, A through D, illustrates embodiments of the invention employing two inner microtubes and an outer microtube.

FIG. 4 illustrates the angle, a, formed by the intersection of the center axis of the inner microtube and a line drawn tangent to the chamfer on the outer wall of the inner microtube.

FIG. 5, A and B respectively, illustrates an alternate embodiment of the invention (controlled asymmetrical flow) and an end section thereof.

FIG. 6 schematically illustrates an alternate embodiment of the present invention (CE/MS extended needle with liquid sheath flow).

FIG. 7 illustrates representative results obtainable by the nebulizer of FIG. 1 under conventional APCI conditions.

DETAILED DESCRIPTION OF THE INVENTION

The invention provides an improved apparatus for reproducibly forming and controlling size and uniformity of droplets from a liquid. The invention provides radial and angular control of sheath fluid flow paths and exit apertures, thereby producing controlled sheath fluid flow velocity and distribution and resultant droplet size and uniformity. The apparatus has a mechanically stabilized inner microtube or needle, which is provided by securing in a predetermined fixed position the inner microtube, such as by narrowing the inner diameter of the outer microtube or otherwise narrowing the annular intermediate space between the inner and outer microtubes for a predetermined length. Thus, the inner microtube is secured in a centered or otherwise predetermined fixed position, with minimum perturbation of the sheath fluid flow. Further, an optional tip, when coupled with a surface at the exit end of the outer microtube, provides a region in which the sheath fluid flow from the outer microtube stabilizes prior to both exiting the tip and colliding with the liquid sample (analyte) exiting the inner microtube.

Broadly, the invention provides an apparatus comprised of at least one inner microtube and an outer microtube, the inner microtube positioned within and surrounded by the outer microtube and defining an inter tube annular intermediate space therebetween. Preferably the inner and outer microtubes are positioned in a concentric arrangement about a common central axis. However, it is operable and in certain embodiments it may be desirable to "offset" the position of the inner and outer microtubes in an eccentric arrangement about substantially parallel axes, such as illustrated in FIG. 5. Each microtube has an exit end and an exit end aperture, through which fluid flows out of each of the microtubes. The liquid sample or analyte flows through the inside of the inner microtube, while the sheath fluid flows inside of the outer microtube and outside of the inner microtube within the annular intermediate space. When more than one inner microtube is used, multiple annular intermediate spaces are formed, wherein more than one sheath fluid or a make-up fluid may be employed.

The outer microtube is adapted so that for at least a portion of its length, the annular intermediate space is reduced to one or more fluid communicating channels and the remainder of the annular intermediate space comprises one or more intermediate structures. The inner microtube is secured in a substantially fixed radial position by providing an intermediate stabilizing brace-like, extension-type, or bridging structure in the annular intermediate space formed between the inner microtube and the outer microtube. The intermediate structure is generally fluid impermeable and extends for a predetermined portion of the length of the outer microtube and mechanically provides support for the inner microtube, stabilizing the inner microtube into a fixed radial position and optionally a fixed axial position. In one embodiment, the brace-like intermediate structure extends inward and contacts the outer wall of the inner microtube. Alternatively, the intermediate structure may be provided by an extension radially outward from the outer wall of the inner microtube contacting or sealably abutting the inner wall of the outer microtube. In still another embodiment, the intermediate structure bridges or spans the annular intermediate space and contacts both the outer wall of the inner microtube and the inner wall of the outer microtube. The annular intermediate space also contains one or more preferably substantially parallel fluid communicating channels continuing lengthwise for a portion of the outer microtube, which permit sheath fluid flow therethrough. In any of the embodiments, the intermediate structure serves the function of stabilizing the inner microtube by restricting radial movement of the inner microtube, while at the same time permitting sheath fluid flow by virtue of a preferably substantially parallel channel or channels communicating with the annular intermediate space on either side of the stabilizing intermediate structure. When more than one inner microtube is employed, generally the outermost inner microtube, that is, the inner microtube closest to the outer microtube, is mechanically stabilized.

As depicted in FIG. 1, a preferred nebulizer assembly in accordance with the present invention comprises an inner microtube 12 having a first exit end aperture and an outer microtube 14 surrounding the inner microtube 12 and defining an inter tube annular intermediate space 24A therebetween. The outer microtube 14 has a second exit end aperture at the same end of the nebulizer assembly and preferably at about the same place as the first exit end aperture of the inner microtube 12. The outer microtube 14 has, for a lengthwise portion 16 of the outer microtube preferably extending up to about 1.1 mm from the second exit end aperture, a reduction of the annular intermediate space to one or more fluid communicating channels (FIG. 1B, 18). The reduction of the annular intermediate space is provided by means of one or more substantially impermeable intermediate structures 20 which extend from the inner wall of the outer microtube 14. The intermediate structure or extension 20 contacts the outer wall of the inner microtube 12 for a predetermined length and functions to mechanically fix in radial position the inner microtube 12. The channel 18 provides the only means for passage of sheath fluid continuing lengthwise along the outside of the inner microtube and provides a continuation of the annular intermediate space between the outer microtube 14 and inner microtube 12 through which sheath fluid may continue to flow after encountering the intermediate structure or extension 20 which effectively narrows the annular intermediate space.

In one preferred embodiment, the invention further provides a tip which, when coupled with a surface at the exit end of the outer microtube, provides a region into which the sheath fluid flow from the outer microtube (restricted to the communicating channels between the intermediate structure) may expand and establish stable fluid flow dynamics (wherein both gas and liquid are termed a fluid for purposes of this invention). Use of such a tip is desirable for the following reasons. Sheath fluid flow within the annular intermediate space prior to encountering the intermediate structure is preferably laminar. Turbulence may occur as the sheath fluid passes through the communicating channel(s). Nebulizing shearing forces would be adversely affected if the sheath fluid flow were not laminar. Therefore, the tip, when coupled to a surface at the exit end of the outer microtube, provides a region into which the sheath fluid may flow and reestablish laminar flow prior to nebulization. The stable (laminar) sheath fluid flow contributes to efficient droplet formation by permitting the energy of the sheath fluid molecules, at the point of nebulization, to pass to the liquid and result in droplet formation, rather than being dissipated in friction inside the microtubes. The tip, upon coupling with a surface at the exit end of the outer microtube, encircles the inner microtube and preferably provides for a length of about 1.0 mm of an annular intermediate space similar to that of the first portion of the outer microtube, providing thereby a buffer space within which the sheath fluid flow can restabilize prior to exiting through the tip orifice.

Figure 1C:
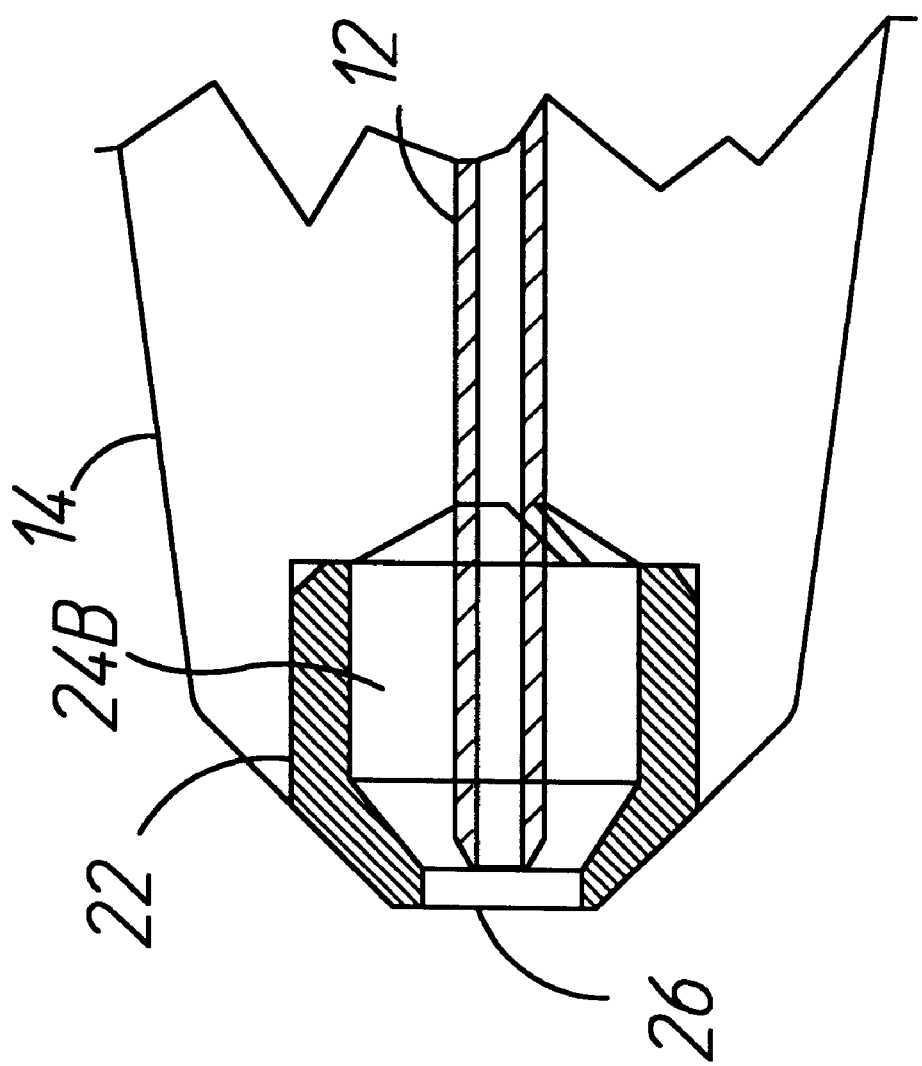

As illustrated in FIG. 1, an insertable cap or tip 22 couples pressably with a surface at the exit end of the outer microtubes 14, encircling the inner microtube 12 and providing an annular intermediate space 24B between the inner wall of the tip 22 and the outer wall of the inner microtube 12 for a length of about 1.0 mm. The tip 22 provides conditions amenable to stabilized fluid (gas or liquid) dynamics, an effective "buffer" region, within which fluid flow may stabilize or optimize prior to exiting through the tip end orifice 26. FIG. 2 illustrates the receiving end 28 of the outer microtube 14 adaptably configured in order to receive the insertable tip 22. Alternately, the tip may be configured as a cap or extendable sleeve (not shown), which mounts onto or over and around the outer microtube 14. However, the insertable tip illustrated in FIG. 2 is preferred for production purposes.

Figure 6:
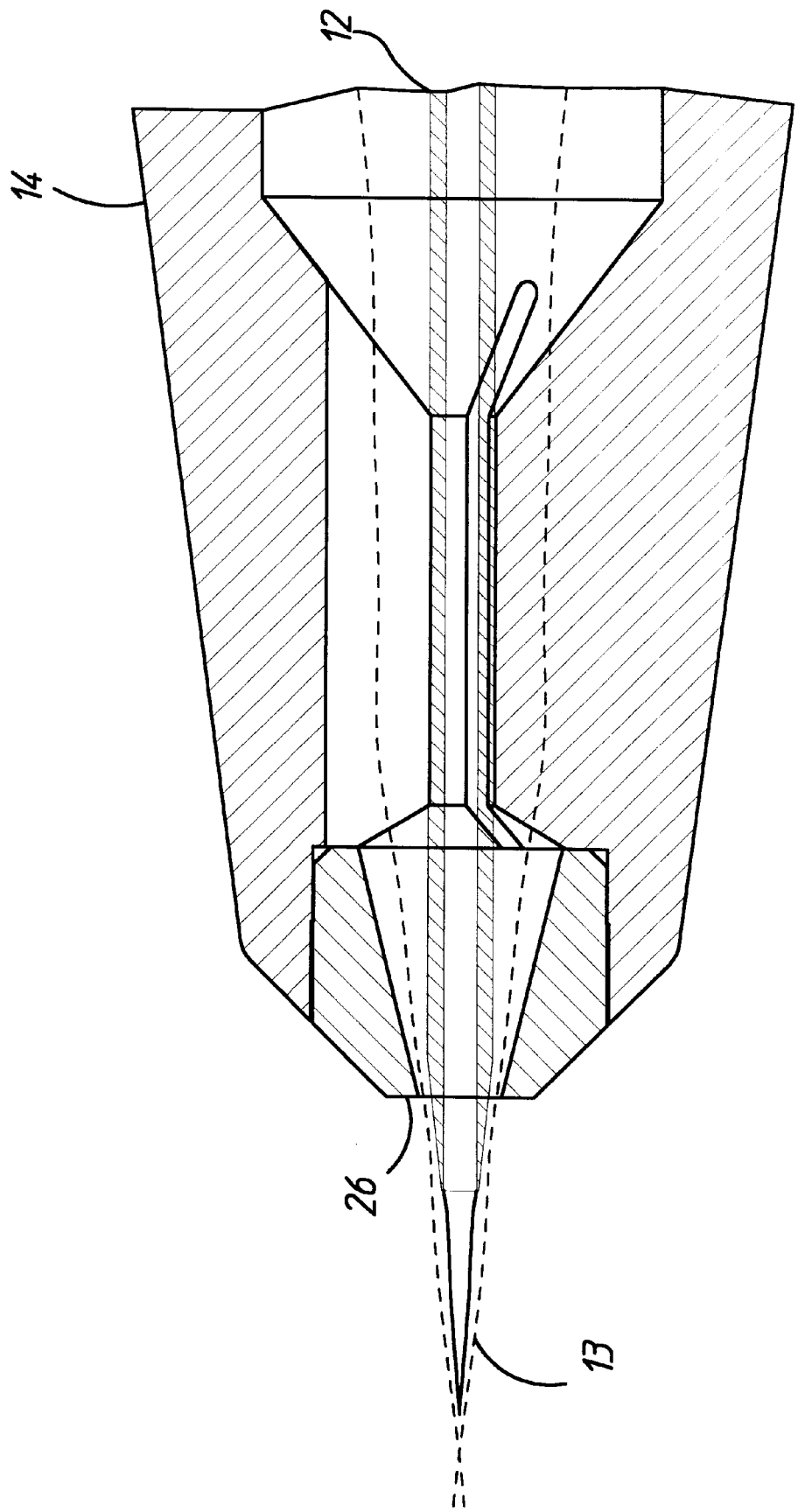

The exit end of the inner microtube may protrude beyond (as illustrated in FIG. 6), be flush with, or be recessed with respect to (as illustrated in FIG. 1) the exit end of the outer microtube. For high liquid sample flowrates, such as typically experienced in APCI-MS applications, the exit end of the inner microtube is preferably recessed with respect to the exit end of the outer microtube. For low liquid sample flowrates, such as typically experienced in CE-MS and some ESI-MS applications, the exit end of the inner microtube preferably is flush with or protrudes beyond the exit end of the outer microtube. In certain embodiments, all, some, or one of the outside surfaces of the tip, the exit ends of the inner microtube(s), and the exit end of the outer microtube, are preferably chamfered, angled, or otherwise tapered. Tapering the inner microtubes may be particularly important with low liquid sample flowrates such as experienced in CE-MS. For example, in CE-MS applications, tapering the inner microtubes assists in focussing the generated electrical field, thus improving sensitivity and stability at low liquid sample flowrates. In certain other embodiments, the position of the inner microtube, while fixed in the radial direction relative to the outer microtube, is adjustable along its longitudinal axis by providing an adjustment means such as a threaded coupling to the inner microtube.

In certain embodiments, more than one inner microtube may be used. In the embodiment illustrated in FIG. 3 (A through D) the nebulizer comprises two inner microtubes. The first inner microtube 30 is positioned within and surrounded by the second inner microtube 32, thus defining a first inter tube annular intermediate space 34 therebetween. The second inner microtube 32 is positioned within and surrounded by the outer microtube 36, thus defining a second inter tube annular intermediate space 38A and 38B therebetween and having four (4) radial communicating channels 44. Each microtube has an exit end and an exit end aperture, through which fluid flows out of each of the microtubes. The liquid sample or analyte flows through the inside of the first inner microtube 30, while a sheath fluid or make-up fluid flows inside of the second inner microtube 32 and outside the first inner microtube 30 within the first annular intermediate space 34. A sheath fluid flows inside of the outer microtube 36 and outside the second inner microtube 32 within the second annular intermediate space 38A and 38B. The embodiment illustrated in FIG. 3 also comprises intermediate structures 40 and a tip 42, as discussed herein above.

Figure 3A:
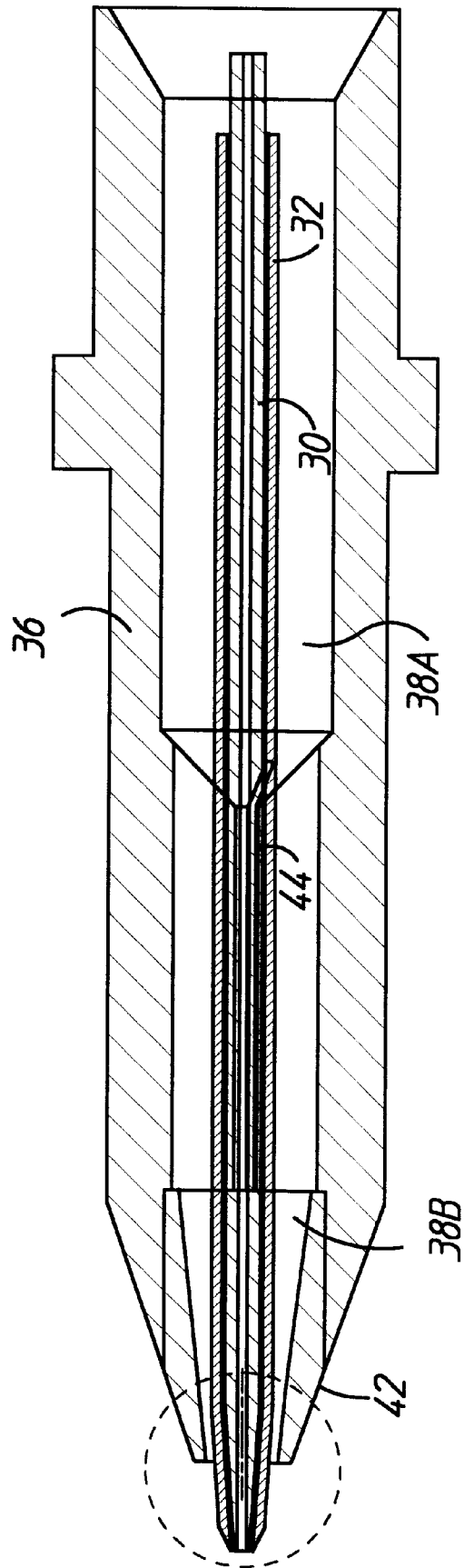
Figure 3B:
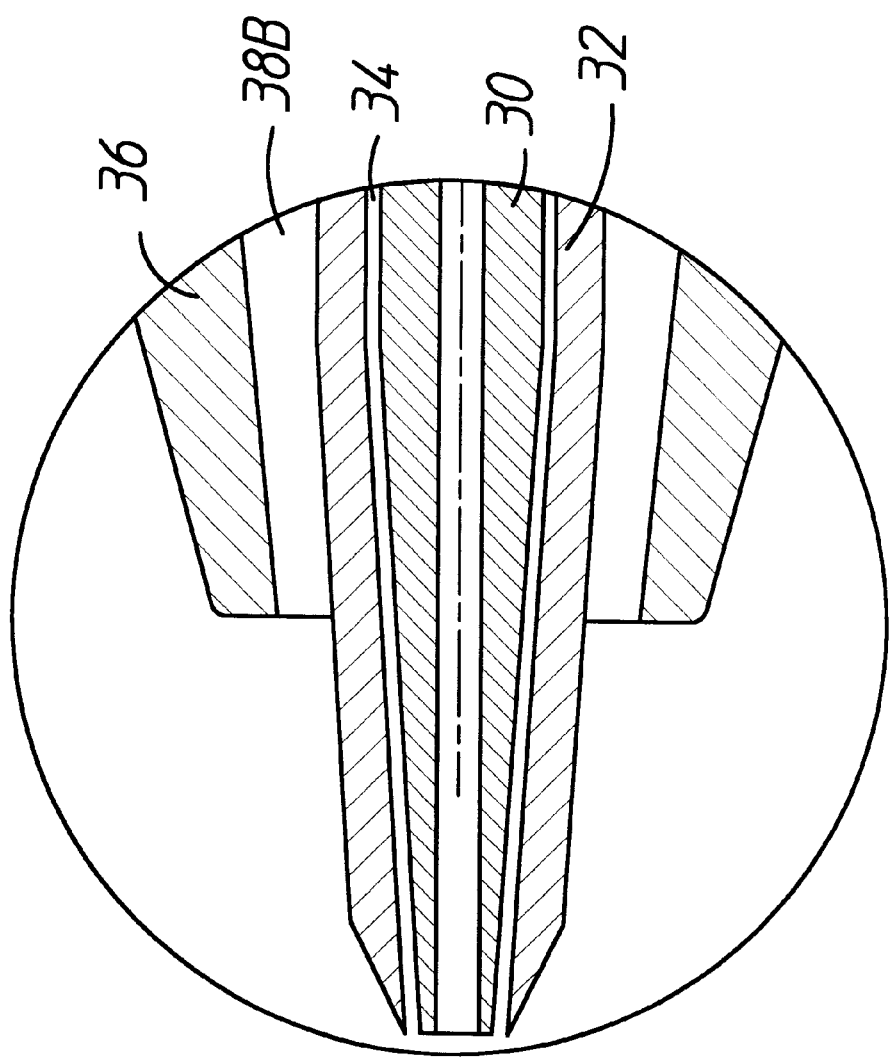
Figure 3C:
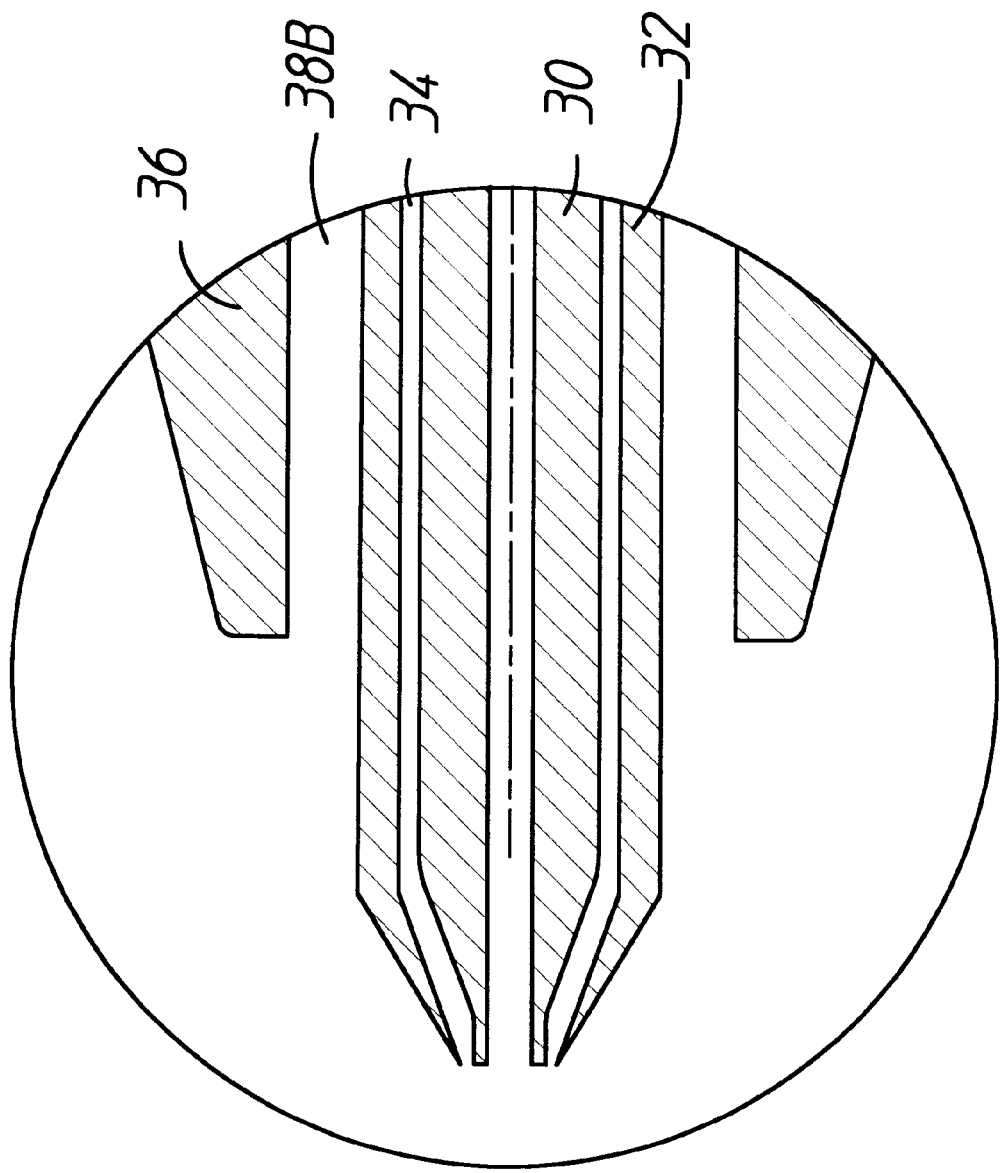

FIG. 3B depicts an enlarged view of the exit end of the nebulizer. The first and second inner microtubes 30 and 32 are tapered to increase the electrical field gradient at the tip 42 in order to assist in Taylor cone formation of the electrosprayed liquid sample. The first annular intermediate space 34 is shown, as well as the details of tapering at the exit ends of the first and second inner microtubes 30 and 32. FIG. 3C depicts an enlarged view of an alternative embodiment using different tapering geometries for the first and second inner microtubes 30 and 32 for easier fabrication, relaxed assembly tolerances, and improved stability. The first inner microtube 30 protrudes from the exit end of the second inner microtube 32 to help initiate the Taylor cone and to avoid signal instability. In a preferred embodiment, the first inner microtube is fabricated from glass and the second inner microtube is fabricated from metal such as stainless steel and serves as the terminating CE electrode. In CE with low liquid sample flowrates, if the first inner microtube were recessed into the second inner microtube, the CE current would cause bubble formation, resulting in undesirable signal instability. Conversely, the maximum acceptable protrusion of the first inner microtube past the second inner microtube is limited by the confines of the sides of the fully formed Taylor cone at the desired liquid sample flowrate.

The embodiment illustrated in FIG. 3 is particularly useful, for example, in CE-MS, wherein make-up fluid, typically a liquid, is employed in the first annular intermediate space 34 and a sheath fluid, typically a gas, is employed in the second annular intermediate space 38A and 38B. As previously disclosed, all, some, or one of the outside surfaces of the tip, the exit ends of the inner microtubes, and the exit end of the outer microtube are advantageously tapered.

Microtubing generally suitable for any currently practiced micro nebulizer may be adapted for the invention herein. For example, in a preferred embodiment, the outer microtube comprises an originally solid stainless steel rod drilled out to an inner diameter of about 1.6 mm on one end to a depth of about 12 mm. The other end of the rod is drilled out to approximately the same inner diameter for a depth of about 1 mm. For the remainder of the intermediate solid rod portion (about 1.6 mm), a center hole is drilled of sufficient diameter to accommodate the inner microtube; multiple channels extending radially, for example three (3) or four (4), are drilled or otherwise machined, optionally each equidistant from the other. Such a geometry may be selected to promote balanced sheath fluid flow, as well as to provide for easy and certain insertion of the needle-like inner microtube into the outer microtube of the nebulizer. The radial openings (see, for example, FIG. 1B) are sufficiently narrow in opening width so as not to permit the inner microtube or needle to pass anywhere but directly into the center hole. Although any suitably refined micro drilling technique may suffice, fine wire electrical discharge machining (EDM) is preferred. Alternately, a plunge quill technique may be used but is slower and more costly.

The invention is not limited to an intermediate stabilizing structure provided by means of drilling out the outer microtube. It is also possible to adapt the inner needle or microtube so as to provide projections from the outside wall of the inner needle or microtube. These projections provide the intermediate structure and the mechanical stabilization and are considered alternate embodiments of the invention taught herein. Microtubes with an intermediate stabilizing structure in the inter tube annular intermediate space by whatever means constructed are considered to be within the scope of the invention claimed herein.

Figure 4:
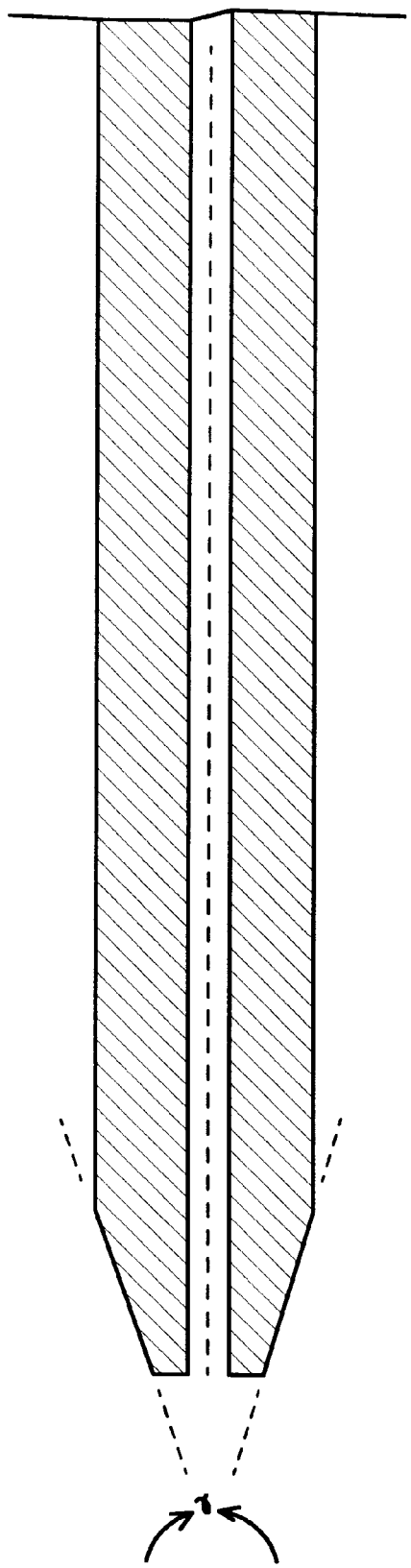

The inner microtube in a preferred embodiment comprises needle gauge stainless steel or fused silica cut to a desired length and chamfered, angled, or otherwise tapered on the outside surface of the tip of the free end. In one preferred embodiment, the inner microtube is, for example, a 33 gauge needle or other microtube device with an inner diameter of about 0.004 inches (0.1 mm). The angling, chamfering, or tapering such as illustrated in FIG. 4 may be accomplished by chemical etching. While any angle or radius less than or about ninety (90) degrees is helpful in directing sheath fluid flow at the exit end aperture, an angle of about thirty (30) degrees performs well in a preferred embodiment. The angle, $\alpha$, is measured by the angle formed by the intersection of the center axis of the inner microtube and a line drawn tangent to the chamfer, angle, or taper on the outer wall of the inner microtube.

The insertable tip (see, for example, FIG. 1C) is also preferably of stainless steel, drilled to be of outer diameter sufficient to press fit into the exit end opening of the outer microtube, for example, an inner diameter of about 0.80 mm to about 0.89 mm, preferably of about 0.84 mm, and an exit orifice. The tip may be hand inserted or a pin vise and V block used; a die and arbor press are preferred for production assembly. Upon insertion, contact is fluid tight and no gas or liquid may pass between the tip and microtube surfaces so contacted.

All dimensions used herein are suggestive and not intended to be restrictive. Appropriate aperture sizes may be any that generally correspond to flow rates useful for nebulization. The relative lengths (microtube, intermediate structure, tip) have been empirically determined. In general, the length of the nebulizer should be as short as is effective, with sufficient tip length to stabilize inert sheath fluid flow after exiting the communicating channel(s) through the intermediate structure. The length of the intermediate structure or length for which the inner diameter of the outer microtube is narrowed is preferably is about four (4) to ten (10) times the diameter of the inner microtube, in order to provide adequate stabilizing of the inner microtube under conditions of operation.

During operation, the liquid sample or analyte flows through the inside of the inner microtube, while the sheath fluid flows inside of the outer microtube and outside the inner microtube within the annular intermediate space. When more than one inner microtube is used, multiple annular intermediate spaces are formed, wherein more than one sheath fluid or a make-up fluid may be employed. Typical flowrates depend upon the application. For example, in ESI-MS and APCI-MS, typical liquid sample flow rates within the inner microtube are in the range of from about 1 microliter/minute to about 2,000 microliters/minute inclusive; sheath fluid flow rates in such applications are typically in the range of from about 2 liters/minute to about 6 liters/minute inclusive. In CE-MS, typical liquid sample flow rates within the inner microtube are less than or equal to about 1 microliter/minute such as about 500 nanoliters/minute to about 1 microliter/minute inclusive. Frequently, however, CE-MS applications will employ nebulizers having at least two inner microtubes providing at least two annular intermediate spaces, the first annular intermediate space providing for make-up fluid flow (typically a liquid) and the second annular intermediate space providing for sheath fluid flow (typically a gas). In such applications, the combined liquid sample and make-up fluid flow rate will typically be less than or equal to about 1 microliter/minute, with sheath fluid flow rates in such applications typically in the range of from about 2 liters/minute to about 6 liters/minute inclusive.

Figure 5A:
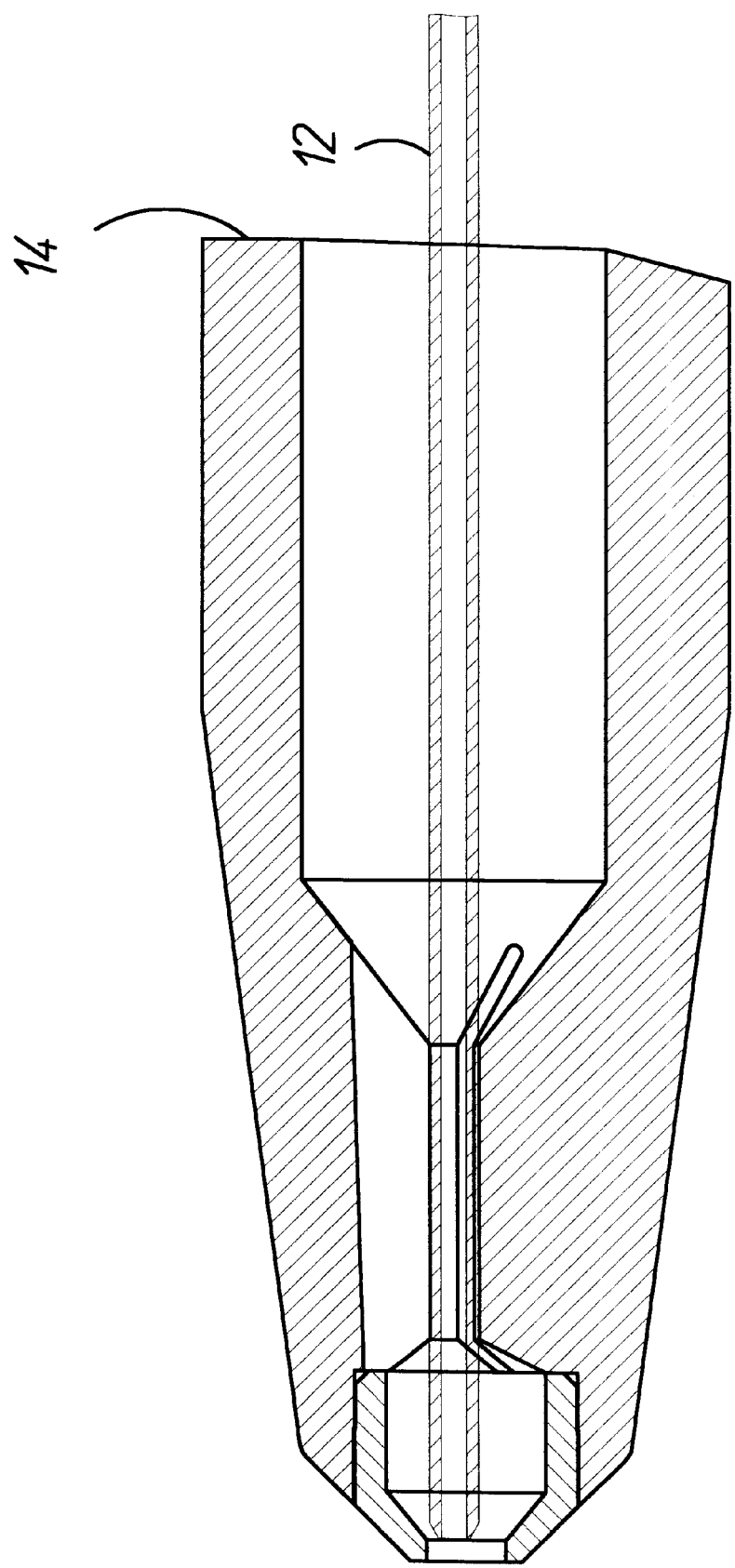
Figure 5B:
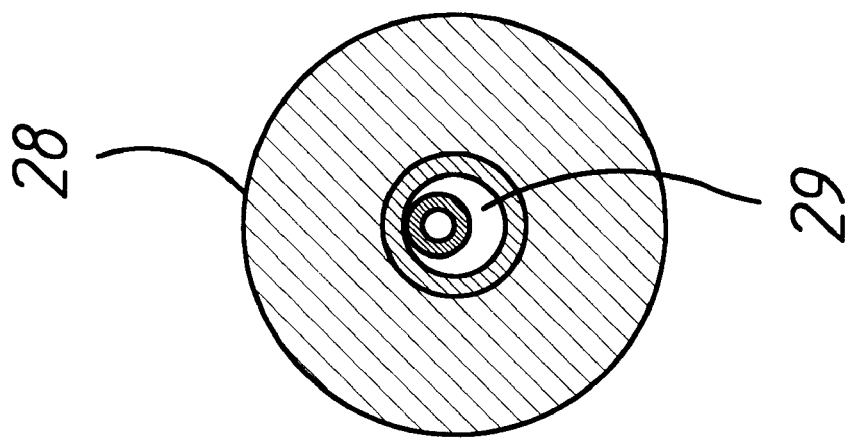

FIG. 5 illustrates an alternate embodiment of the invention taught herein referred to as "controlled asymmetry". In some applications, only a portion of the eluent will be analyzed rather than the entire sample. In such applications, only a controlled portion of the droplets produced need be fine, but it is desirable to controllably create reproducibly fine droplets for analysis. FIG. 5B illustrates an end-view of asymmetrically drilled exit aperture 28 and internal stabilizing elements (not shown). In operation, the gas velocity is greatest in the widest gap portion of the aperture 29, and there the sheath gas will shear the liquid so as to generate the finest droplets. Droplets located on that side of the exiting plume will be selected for analysis, and all others droplets will pass by.

FIG. 6 illustrates an alternate embodiment of the invention taught herein, namely, a configuration useful in CE/MS. In CE/MS, the outer microtube conducts, not a sheath gas as in most other nebulizer applications, but a sheath liquid. The inner microtube is fabricated from a nonconducting material. The sheath liquid in the outer microtube 14 encounters the analyte liquid at the exit end aperture, where the sheath liquid completes the electrical contact for the analyte liquid and permits the analyte to migrate out of the inner microtube and into the sheath liquid. The sheath liquid, carrying the migrated analyte, forms a Taylor cone. In such a CE/MS embodiment, the mechanical stability imparted by the invention provides stable liquid flow across the tip and results in stable Taylor cone formation. Instability in flow and/or in the Taylor cone impairs performance and produces erratic signal, signal drop out, noise, or any combination of performance problems. In FIG. 6, a protruding inner needle 13 portion is depicted. The needle protrusion is not essential to CE/MS but is useful in assisting Taylor cone formation.

FIG. 7 represents results obtainable by the invention taught herein in an APCI application. The line indicating droplet size 72 indicates the improvement over prior art nebulizer performance 70.

The apparatus described above may be coupled to any analytical system in order that droplets produced by the apparatus may be analyzed. The apparatus of this invention provide a useful interface for analytical systems based on techniques such as mass spectrometry (MS), atomic absorption (AA), or inductively coupled plasma (ICP) which cannot directly analyze liquid samples. In a preferred embodiment, the apparatus is coupled to a mass spectrometer. Any suitable mass spectrometer may be used, for example quadrupole or multipole, magnetic or electric sector, Fourier transform, ion trap, and time-of-flight mass spectrometers. The invention is particularly useful as part of an interface for mass spectrometers employing, for example, electrospray ionization (ESI) or atmospheric pressure chemical ionization (APCI) to analyze liquid samples.

While this invention has been described with reference to several embodiments, it is contemplated that various alterations and permutations of the invention will become apparent to those skilled in the art upon a reading of the preceding descriptions and a study of the drawings. It is therefore intended that the scope of the present invention be determined by the following appended claims.

What is claimed is:

1. An apparatus for forming droplets from a liquid comprising:

A. at least one inner microtube having an outer wall, an exit end, and an exit end aperture, B. an outer microtube having an inner wall, an exit end, and an exit end aperture, wherein the inner microtube has an outer diameter smaller than the inner diameter of the outer microtube, and the inner microtube is positioned within and is surrounded by the outer microtube such that an annular intermediate space is formed therebetween, with the exit end of each microtube being located at a same end of the apparatus, and wherein the exit end of the inner microtube is flush with respect to the exit end of the outer microtube, C. one or more intermediate structures either (i) extending inward radially from the inner wall of the outer microtube and contacting the outer wall of the inner microtube for a predetermined length, (ii) extending outward radially from the outer wall of the inner microtube and contacting the inner wall of the outer microtube for a predetermined length, or (iii) spanning the annular intermediate space and contacting both the outer wall of the inner microtube and the inner wall of the outer microtube for a predetermined length, wherein the intermediate structure is situated so as to mechanically stabilize the inner microtube, and D. one or more communicating channels continuing lengthwise along the outside of the inner microtube, wherein the communicating channel provides a continuation of the annular intermediate space and through which a fluid may continue to flow after encountering the intermediate structure.

2. An apparatus for forming droplets from a liquid comprising:

A. at least one inner microtube having an outer wall, an exit end, and an exit end aperture, B. an outer microtube having an inner wall, an exit end, and an exit end aperture, wherein the inner microtube has an outer diameter smaller than the inner diameter of the outer microtube, and the inner microtube is positioned within and is surrounded by the outer microtube such that an annular intermediate space is formed therebetween, with the exit end of each microtube being located at a same end of the apparatus, and wherein the exit end of the inner microtube protrudes beyond the exit end of the outer microtube, C. one or more intermediate structures either (i) extending inward radially from the inner wall of the outer microtube and contacting the outer wall of the inner microtube for a predetermined length, (ii) extending outward radially from the outer wall of the inner microtube and contacting the inner wall of the outer microtube for a predetermined length, or (ii) spanning the annular intermediate space and contacting both the outer wall of the inner microtube and the inner wall of the outer microtube for a predetermined length, wherein the intermediate structure is situated so as to mechanically stabilize the inner microtube, and D. one or more communicating channels continuing lengthwise along the outside of the inner microtube, wherein the communicating channel provides a continuation of the annular intermediate space and through which a fluid may continue to flow after encountering the intermediate structure.

3. A nebulizer assembly, comprising:

A. a first inner microtube having an exit end and an exit end aperture,

B. a second inner microtube having an exit end and an exit end aperture, wherein the first inner microtube has an outer diameter smaller than the inner diameter of the second inner microtube, and the first inner microtube is positioned within and is surrounded by the second inner microtube such that a first annular intermediate space is formed therebetween, C. an outer microtube having an exit end adapted for coupling with a tip and an exit end aperture, wherein the second inner microtube has an outer diameter smaller than the inner diameter of the outer microtube, and the second inner microtube is positioned within and is surrounded by the outer microtube such that a second annular intermediate space is formed therebetween, with the exit end of each microtube being located at a same end of the nebulizer assembly, and D. a tip which couples with a surface at the exit end of the outer microtube, thereby forming a region near the exit ends of the microtubes within which fluid may stabilize;

wherein the inner diameter of the outer microtube is narrowed for a predetermined portion of its length such that the second annular intermediate space is reduced to one or more fluid communicating channels.

4. The nebulizer of claim 3, wherein at least one of the first inner microtube, the second inner microtube, the outer microtube, and the tip has an outer surface which is chamfered, angled, or tapered.

5. The nebulizer of claim 3, wherein the first inner microtube, the second inner microtube, and the outer microtube each has an outer surface which is chamfered, angled, or tapered.

6. A mass spectrometer system comprising the nebulizer of claim 3.

* * * * *